United States Patent [19]

Harrison

[11] 4,139,458

[45] Feb. 13, 1979

[54] PREPARATIVE CENTRIFUGAL CHROMATOGRAPHY DEVICE

[76] Inventor: Shuyen Harrison, 840 Moana Ct., Palo Alto, Calif. 94306

[21] Appl. No.: 838,946

[22] Filed: Oct. 3, 1977

[51] Int. Cl.² .............................................. B01D 15/08
[52] U.S. Cl. ................................ 210/31 C; 210/198 C
[58] Field of Search .......... 210/31 C, 198 C, 360–368; 118/109–112, 256, 558; 55/400, 406, 40, 17

[56] References Cited

U.S. PATENT DOCUMENTS

| | | | |
|---|---|---|---|
| 1,505,564 | 8/1924 | Jett | 55/406 X |
| 2,986,280 | 5/1961 | Magnuson | 210/198 C |
| 3,113,103 | 12/1963 | Lowery | 210/198 C |
| 3,194,400 | 7/1965 | Herndon | 210/203 |
| 3,229,505 | 1/1966 | Sanford et al. | 210/31 C |
| 3,511,695 | 5/1970 | Wright | 118/111 |
| 3,617,557 | 11/1971 | Giltrow | 210/31 C |
| 3,915,856 | 10/1975 | Meyer | 210/31 C |
| 3,919,082 | 11/1975 | Falk | 210/31 C |
| 3,994,805 | 11/1976 | Ito | 210/31 C |

OTHER PUBLICATIONS

Deyl, Rosmos, and Pavlicek, *Centrifugal Chromatography*, pp. 20–52.
Journal of Chromatography, 66 (1972), *The Chromatofuge*, pp. 365–369.
Chemical Abstracts, vol. 69, p. 54584m, Centrifugal Chromatography, 1968.

*Primary Examiner*—John Adee
*Attorney, Agent, or Firm*—Geoffrey L. Chase; Martin P. Hoffman

[57] ABSTRACT

An apparatus and method for preparative separation and collection of the components of a mixture by the use of a thin layer preparative centrifugal chromatography device in which a rotor mounted for rotation supports a thin layer of absorbent material used to separate the components of a mixture and a juxtaposed annular collection trough canted at an angle to the horizontal plane collects the separated and eluted components by means of a deflection surface canted toward the axis of rotation of the rotor at an angle of less than 90° to the plane of the rotor. The chromatography device alternately consists of a series of rotors. The absorbent layer supported on the rotor is prepared by means of a chromatographic scraper device.

18 Claims, 9 Drawing Figures

PREPARATIVE CENTRIFUGAL CHROMATOGRAPHY DEVICE

BACKGROUND OF THE INVENTION

This invention relates to that field of chromatography which uses thin layer absorbent mediums, such as paper, ion exchange medium, silica gel, glass fiber-silica gel composites or similar material and high speed rotational chromatographic devices utilizing centrifugal force to decrease the amount of time required to separate compounds and increase the volume and the resolution of the compounds so separated. In another aspect, the invention relates to methods for separating compounds using the above device and to apparatus for preparing the absorbent surface on a chromatographic rotor.

Chromatography, generally, relates to the separation of a multi-component mixture by the differential passage of the components of the mixture through an absorbent medium, with the assistance of a solvent, by means of capillary action, gravity, pressure or centrifugal force.

This invention specifically relates to preparative thin layer centrifugal chromatography. Preparative chromatography is concerned with the separation and recovery of a considerable quantity of the components of a mixture. Thin layer chromatography is directed to the use of a thin layer of absorbent medium on a supporting surface of absorb and seaprate a mixture. Centrifugal chromatography relates to the use of strong centrifugal forces to improve the chromatographic separation of the components of a mixture. This invention utilizes all three concepts to provide a novel apparatus and method for producing improved chromatographic results.

The preparative centrifugal chromatography device of this invention is distinguished from analytical centrifugal chromatography devices in that the present invention is directed to separation and recovery of a volume of a mixture component, whereas analytical centrifugal chromatography devices are only concerned with the separation of the mixture on the absorbent medium for analysis there on. Such analytical devices are not presented with the problems of chromatographic collection as in the present invention.

Centrifugal chromatography devices have been known in the prior art. These devices generally consist of rotors or discs upon which a mixture to be separated is placed. The rotor or disc is spun at sufficient speeds to develop centrifugal forces, which assist in separating the applied mixture. The prior art chromatographic devices, however, suffer from several serious disadvantages which impair their use in both commercial and research facilities. Specifically, prior art devices cannot be used in high speed operation wherein significant centrifugal forces are available. Such devices also fail to allow for continuous operation and collection of separated components of a mixture. Additionally, the prior art devices cannot be used to collect appreciable quantities of a separated component or further resolve closely spaced components. The prior art devices have also not dealt effectively with the spattering of separated and eluted components as they fly off the outer edge of the rotor or disc of the chromatographic device. Finally, the prior art devices have not solved the problem of producing uniform absorbent mediums on the chromatographic rotor or disc surface.

SUMMARY OF THE INVENTION

In the present invention, the shortcomings of the prior art chromatographic devices are overcome and significant advantages, heretofore unrealized, are achieved.

It is an object of the present invention to reduce the time required to separate components of a mixture and at the same time to increase the quantity of the components separated without destroying the quality of the separation during the collection process.

Another object of the present invention is to fully elute the separated components to facilitate continual operation and thus avoid either, the disassembly of the device in order to provide a clean rotor for a new run or the destruction of the absorbent medium in order to recover the desired component.

Further objects of the present invention are to increase the resolution of normally closely resolved components and to provide more uniform and precise absorbent layers on the rotor of the chromatography device.

The preferred embodiment of the preparative centrifugal chromatography device of the present invention comprises an annular chamber canted at an angle to the horizontal plane. A rotor, consisting of a generally flat disc with an absorbent medium coated on its upper surface is mounted for rotation within the annular chamber. The rotor is also canted at an angle to the horizontal plane. An annular collection trough for receiving components which have been separated chromatographically is positioned on the radially inner surface of the wall of the annular chamber adjacent the outer edge of the rotor and canted at an angle to the horizontal. The collection trough has a deflection surface which is canted toward the axis of rotation of the rotor and forms an angle of less than 90° with the upper surface of the rotor. An exit tube is located at the lowermost point of the collection trough to continually remove the separated components from the device to a suitable receptacle.

The chromatography device alternately consists of a number of axially spaced rotors and corresponding collection troughs. The collection troughs feed the separated components in series from the collection trough drain of one rotor system to the center of the next rotor for further separation in a continual operation, until the components have passed through each of the axially spaced rotor assemblies.

The invention also includes a detachable scraper device for providing a uniform absorbent medium layer on the upper surface of the rotor of the chromatographic device. The scraper device consists of a scraper blade mounted on adjustable, rod-like pins. The scraper blade is supported at the circumferential edge of the rotor by one pin and is supported at its opposite end, near the axial region of the rotor, by a perpendicularly attached brace plate. The brace plate is centrally bored to fit over the rotor drive shaft and is, itself, supported at its opposite ends by adjustable pins.

The preparative centrifugal chromatography device is operated by introducing a mixture to be separated to a point at the radially inner top surface of the rotor, followed by the introduction of a solvent or carrier for the mixture to the rotor. The revolving rotor provides strong centrifugal forces which assist in the differential migration of the solvated components outward through the absorbent medium to the circumferential edge of the rotor. The separated components are thrown off the rotor and collect in the collection trough, where the components drain by force of gravity to the exit tube located at the lowermost point of the collection trough.

DETAILED DESCRIPTION OF THE INVENTION

Figure 1:
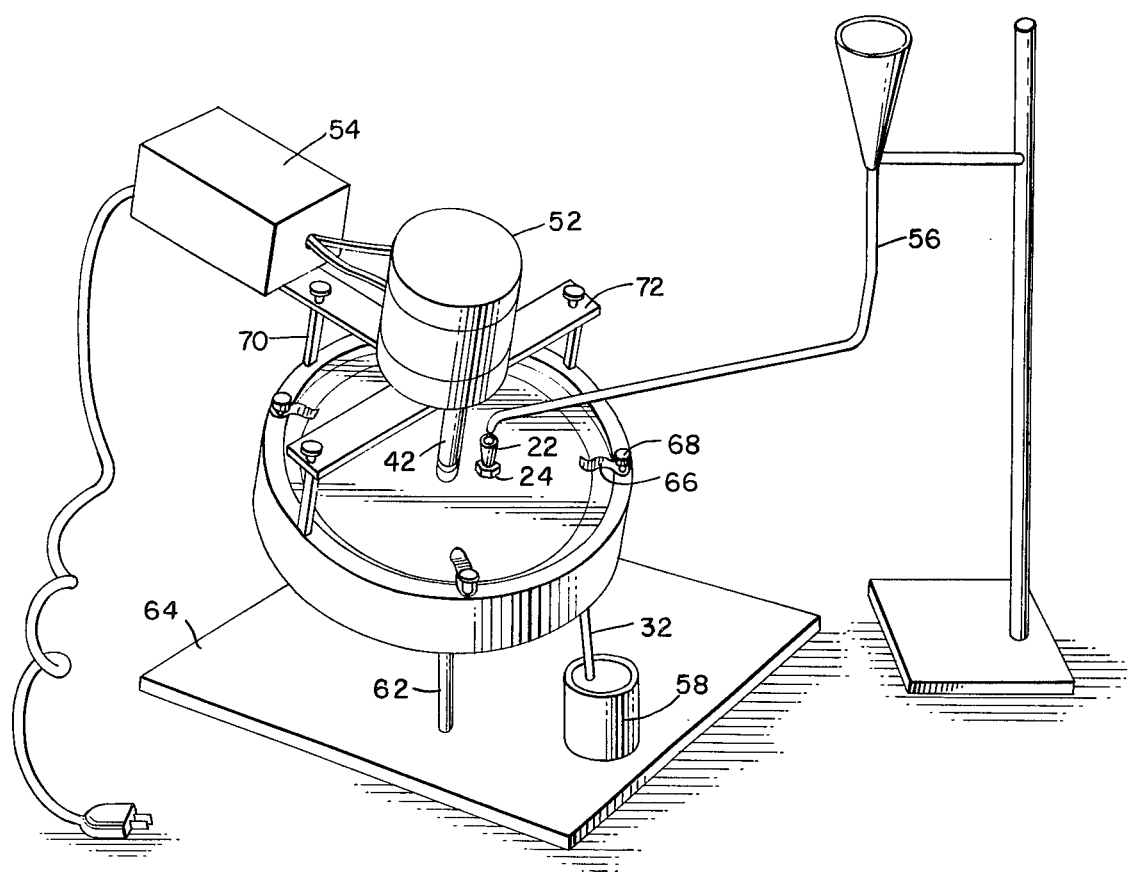
FIG. 1 is a perspective view of the apparatus embodying this invention along with a funnel feed which may be used with the invention.
Figure 2:
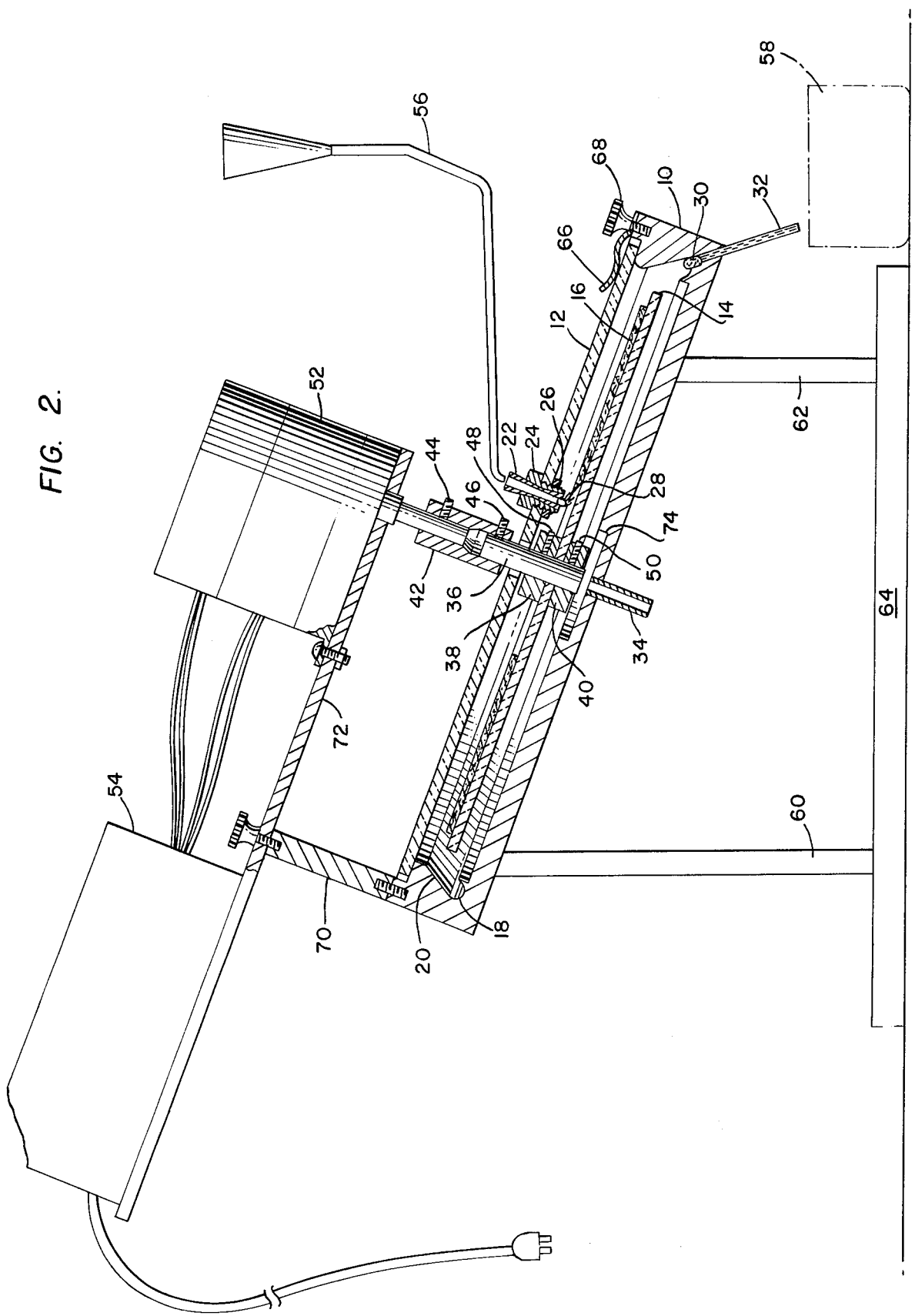
FIG. 2 is a side view, in partial section, of the apparatus of this invention.

The structure and the operation of the preparative centrifugal chromatography device of the present invention is best described by referring to FIGS. 1 and 2. The novel device consists of a rotor 14 which is a flat circular disc attached to a rotor shaft 36 by means of disc collars 38 and 40. The disc collars are adjusted on the shaft 36 by means of set screws 48 and 50. The rotor 14 carries an absorbent medium 16 on its upper surface. The rotor 14, which is canted at an angle to the horizontal plane, is designed to revolve within an annular chamber 10 which is supported on a number of legs, shown as 60 and 62. The annular chamber 10, which is canted at an angle, preferably, between 15° to 25° to the horizontal, has a collection means consisting of a trough 18 formed in the radially inner surface of the wall of the chamber 10. The collection trough 18 is canted at the same angle as the annular chamber 10 and the rotor 14. The collection trough includes a radially outer deflection surface 20 which is canted toward the axis of rotation of the rotor 14 forming an angle of less than 90° with the upper surface of the rotor. Preferably, the angle is between 45° and 60° although angles of 20° to 75° are acceptable. An exit tube 32 is provided at the lowermost point of the collection trough 18 and functions to drain separated and eluted fluids from the collection trough 18 through the annular chamber 10 to suitable receiving receptacle 58. An absorbent plug 30 is placed in the collection trough end of the exit tube 32 to control the drainage of the eluted components.

A sump 74 is provided in the base of the annular chamber 10 to collect run off fluids and allow for clearance of the lower rotor collar 40. A tubular inlet 34 is formed in the center of the sump 74. This inlet is used to introduce a dry gas to the interior of the chromatography device either during operation of the chromatographic separation process, so as to provide an inert atmosphere, or after the process has been completed, so as to evaporate solvents used to clean the absorbent medium of any residual materials before another chromatograhic operation is performed. Any suitable gas may be supplied to inlet 34, such as nitrogen gas.

A cover 12, preferably made of a transparent material which is unaffected by the materials used in the chromatographic separations, such as glass, is placed over the top of the annular chamber 10. The cover 12 is designed to allow the rotor shaft 36 to pass through it without hinderance to the rotation of the rotor shaft 36. The cover 12 is held in place by a number of spring clip and thumb screw combinations, 66 and 68 respectively, which hold the cover 12 against the annular chamber 10.

An aperture is located near the axial center of the cover to accept a filling means consisting of a tapered tube 22 held in a threaded insert and nut combination, 24 and 26 respectively, which is fastened in the cover. A wick 28 is provided at the lower end of the tapered tube 22. This wick 28 acts to supply the sample fluid mixture to be separated chromatographically to the rotor assembly in a more uniform, even flow than would be possible in the direct application of a fluid to the rotor. A funnel with a long drain tube 56 is shown supplying the sample fluid mixture to the tapered tube 22, but this is in way of illustration only, and in practice, any suitable supply means is sufficient for the operation of the device.

The rotor shaft 36 of the chromatography device is connected, by means of a drive connector 42 and appropriate set screws 44 and 46, to a rotational power source, which consists of a motor 52 capable of controlled uniform rotational speeds. The preferred motor is an electric motor which can be controlled by a suitable means, such as control box 54. The motor 52 is supported on a "T" shaped motor mount 72 which in turn is connected to the annular chamber 10 by means of three support arms 70.

Figure 5:
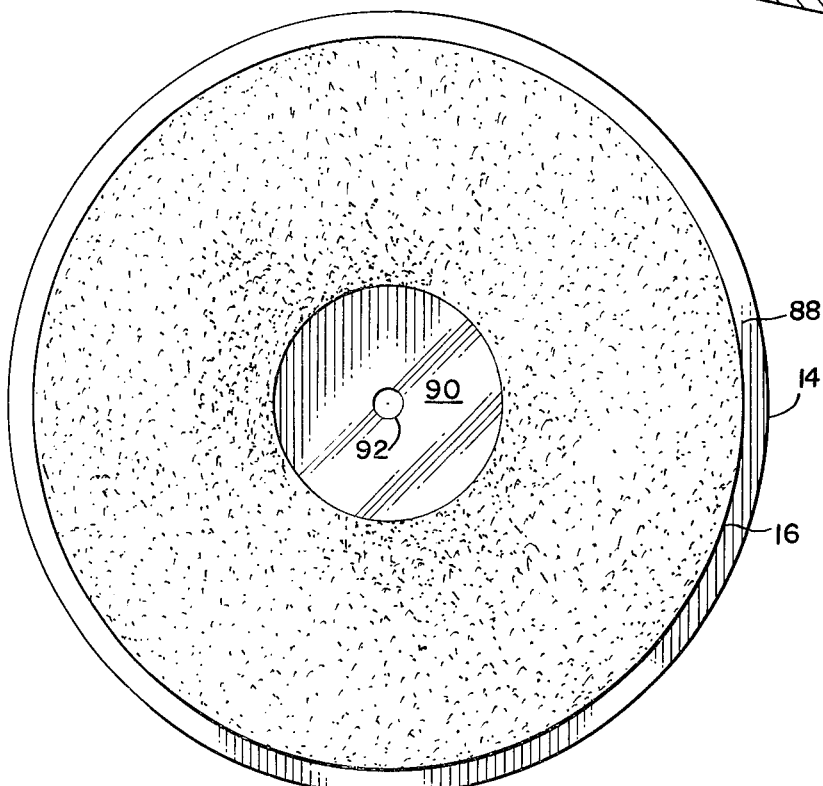
FIG. 5 is a plane view of the rotor with the prepared absorbent surface of the present invention.

FIG. 5 shows the prepared top surface of the rotor 14 used in the present chromatography device. The rotor consitutes a flat circular disc with a central axial bore 92 through which the rotor shaft 36 passes. The upper surface of the rotor has a precisely flat surface upon which an absorbent medium is applied. It is important that the surface does not vary significantly from the true plane of the rotor surface because of the effect such variations would have on the radially outward flow of the solvated sample mixture during a chromatographic separation. In order to effect the development of uniform concentric bands of separated mixture components emanating from the radially inner portion of the rotor surface, it is important that the components pass through an equal amount of absorbent medium 16. Maintenance of an even amount of absorbent medium, through which the solvated components pass, is directly affected by two factors: the flatness of the rotor surface and the application of a uniform absorbent medium to the rotor surface.

Where the absorbent medium is a preformed disc supported on the rotor, such as chromatography paper or a glass fiber-silica gel composite, the characteristics of such a preformed disc are the most important factor in maintaining uniformity of the absorbent through which the solvated components pass. However, where, as in the preferred embodiment of this invention, the absorbent medium is incorporated in a slurry, such as an aqueous suspension of silica gel with calcium sulfate, which is applied to the rotor surface with the aid of a binder, and then dried, the evenness of the absorbent medium layer will depend on the development of a uniform layer, either during the coating operation, or thereafter by the removal of the excess buildup of the absorbent.

Regardless of the type of absorbent used, the rotor surface is prepared so that the absorbent does not cover the axial surface 90 and, also, does not cover the outer peripheral surface 88 which forms the outermost concentric area of the rotor. This peripheral, cleaned surface 88 prevents disturbance of the outer edge of the absorbent layer when the rotor is being placed within the chamber.

In operation, the preparative centrifugal chromatography device is made ready for separations by preparing the rotor with an absorbent medium on its upper surface. With the rotor revolving at a predetermined speed, a solution of the mixture to be separated in a small amount of solvent is added via the tapered tube 22. It is transferred to the upper surface of the rotor at a controlled rate by the wick 28. After application of the sample mixture, the solvent for resolution and elution is added continuously via the same tapered tube and wick as the sample. As the rotor turns and the solvent carries the components of the sample mixture into the absorbent medium, the components separate into circular bands concentric with the rotor and move outward at different rates by means of the capillary action of the absorbent and the strong centrifugal forces imparted by the revolving rotor. The concentric bands of components then are ejected, together with solvent, from the edge of the rotor and impact against the deflection surface of the collection trough. The deflection surface directs the fluid down into the channel portion of the collection trough. The continuous spray of impinging droplets on the downward and outwardly sloping deflection surface aids in insuring that all portions of the separated band of a component are forced down into the collection trough in the proper sequence, so that remixing due to hangup or spattering of droplets does not occur. From the collection trough, which is canted at an angle to the horizontal plane, the separated and eluted components quickly run by gravity down to the lowermost point of the collection trough, where they are removed via the exit tube to a suitable receptacle. A detection means, optical for colored components, ultraviolet absorption or refractive index for colorless components, is situated at the exit tube in order to detect the passage of certain fractions or components and, therefore designate when to change the receptacle into which a particular draining component passes to avoid remixing of components.

The device is made ready for further separations by adding acetone, methanol or other polar volatile solvents in place of the eluting solvent, thus removing impurities and water remaining on the absorbent medium. After evaporation of this solvent by means of an inert gas, such as nitrogen, introduced at the tubular inlet 34 under the device with the rotor in motion, the device is ready for further separations using the same regenerated absorbent medium.

Known techniques for improving the separation can also be applied to the present device. For example, the output from the device can be pumped to the input in order to recycle the eluant and separating components. Additionally, the solvent can be partially evaporated for a period of time during the recycling process by passing an inert, dry gas into the device via the tubular inlet 34, thereby reducing the width of the separating bands of components.

The preparative centrifugal chromatography device is designed to operate at rotational speeds of the rotor between 100 and 10,000RPM, although the preferred range is from 300 to 1,800 RPM. Because of the high tangential speeds imparted to the solvated component droplets by such rotor speeds, it is essential to provide a non-spattering collection trough such as is contemplated by the deflection surfaces of the present invention. Comparisons of such a deflecting surface with a vertical deflection surface and a radially outward canted deflection surface have shown that the radially inward canted deflection surfaces of the present invention produce negligible spattering and actually utilize impinging droplets to force previously deposited eluant quickly into the channel of the collecting tough, while the vertical and radially outward canted deflection surfaces create significant spattering and attendant intermixing of eluant droplets, in addition to the lack of the draining effect of impinging, subsequently eluted, droplets. This unique feature of the collection trough of the present invention, along with the canting of the collection trough to the horizontal plane, produces the novel utility of the present device, which provides a practical tool for the separation of complex mixtures and large volume mixtures.

Figure 3:
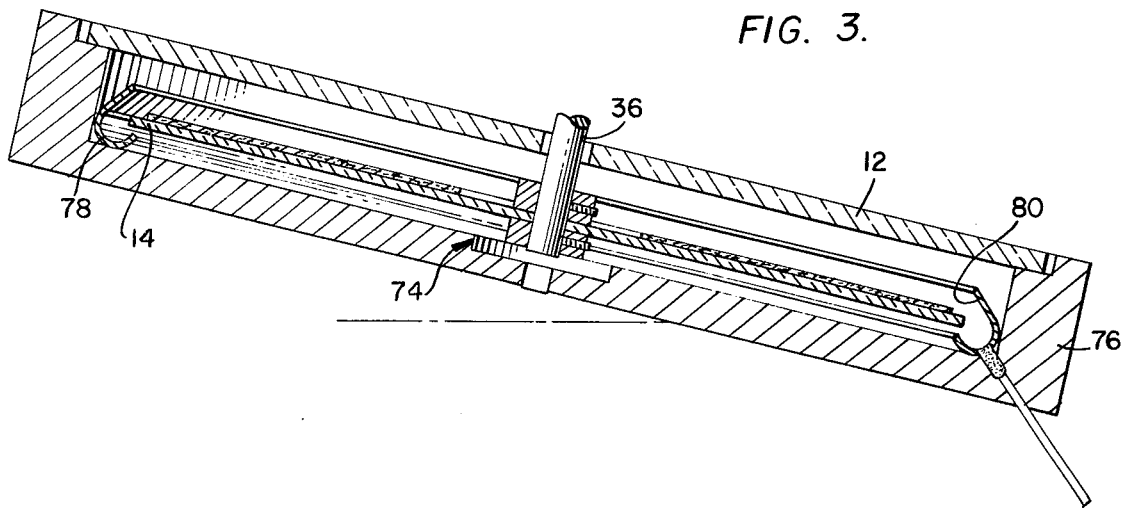
FIG. 3 is a fragmentary view, in partial section, for an alternate embodiment of the collection trough of the present invention.

FIG. 3 shows an alternate embodiment of the collection means of the present invention. The collection means 78, which is canted at an angle to the horizontal plane, consists of an annular collection trough positioned radially inward of the wall of the annular chamber 76. The trough is constructed of a sheet material formed into a circular gutter having a generally "U" shaped cross section. The outer wall of the trough extends beyond the upper surface of the radially inner wall and is canted axially inward at an angle less than 90° to the plane generally described by the collection trough, so as to form a deflection surface 80. This deflection surface directs eluted components from the rotor down into the channel of the trough, where the components quickly drain by force of gravity to the exit tube at the lowermost point of the collection trough.

Figure 4:
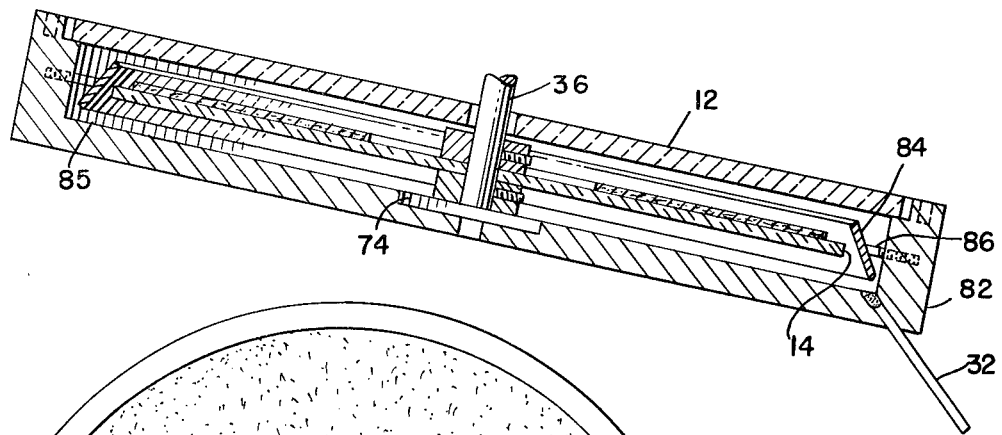
FIG. 4 is a fragmentary view, in partial section, of another alternate embodiment of the collection trough of the present invention.

FIG. 4 shows yet another embodiment of the present invention. The annular collection means, which is canted at an angle to the horizontal plane and attached to the annular chamber 82 by mounting pins 86, consists of a deflection surface 84 without a channel or trough structure. The deflection surface 84 is canted axially inward at an angle of less than 90° to the plane formed by the upper surface of the rotor 14. Droplets of eluted material from the rotor impinge against the deflection surface and drain down to the lower edge 85 of the surface from which they then drain by gravity along the lower edge 85 until they accumulate at the lowermost point of the deflection surface, where they drain through the exit tube 32.

Figure 6:
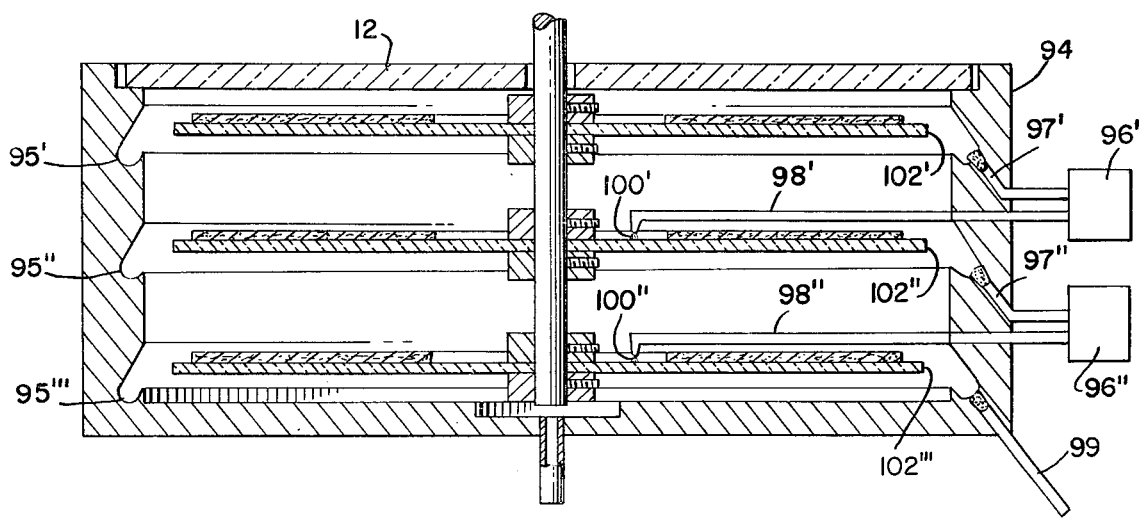
FIG. 6 is a fragmentary view, in partial section, of another alternate embodiment of the present invention.

The embodiment of the preparative centrifugal chromatography device shown in FIG. 6 can be used to increase the quality of separation of complex mixtures. The device consists of an annular chamber 94 having an axially spaced series of annular collection means consisting of troughs 95', 95" and 95'" designed individually like the trough 18 of FIG. 2. The troughs consist of integral channels formed in the radially inner surface of the chamber wall, as shown in FIG. 6, or the collection means alternately consist of a spaced series of the collection means shown in FIGS. 3 or 4. Although a series of three collection trough and corresponding rotors are shown in FIG. 6, it is understood that any number of rotors and collection devices utilized in a series is within the contemplation of the present invention. As shown in FIG. 6, adjacent each collection trough is a corresponding rotor 102', 102" and 102''' which performs the same function of centrifugally assisting chromatographic separations as described in the device shown in FIG. 2. However, as the separated components of the sample mixture placed on the rotor 102' are eluted to the uppermost annular collecting means 95' and drain to exit tube 97', they are cycled by suitable pumping means 96' through tube 98' to a point at the radially inner top surface of the corresponding next lower rotor 102". Correspondingly, the components, as they are eluted from the central rotor 102" to the central annular collecting means 95" and are drained through exit tube 97", are cycled by pump 96" to the radially inner top surface of rotor 102''', the lowest rotor. The separated components of the sample mixture from this rotor 102''' are eluted to the lowest collecting means or trough 95''' and pass out of the annular chamber 94 by way of exit tube 99, where they are collected in a suitable receptacle, not shown in the drawing. The collection trough, as well as the rotors and annular chamber of this series chromatography device, are canted at an angle to the horizontal plane in order to quickly drain the eluant from the collection troughs. This series chromatography device performs better separations, particularly on complex mixtures in which the components would normally be closely separated, than a single rotor chromatography device.

Figure 7:
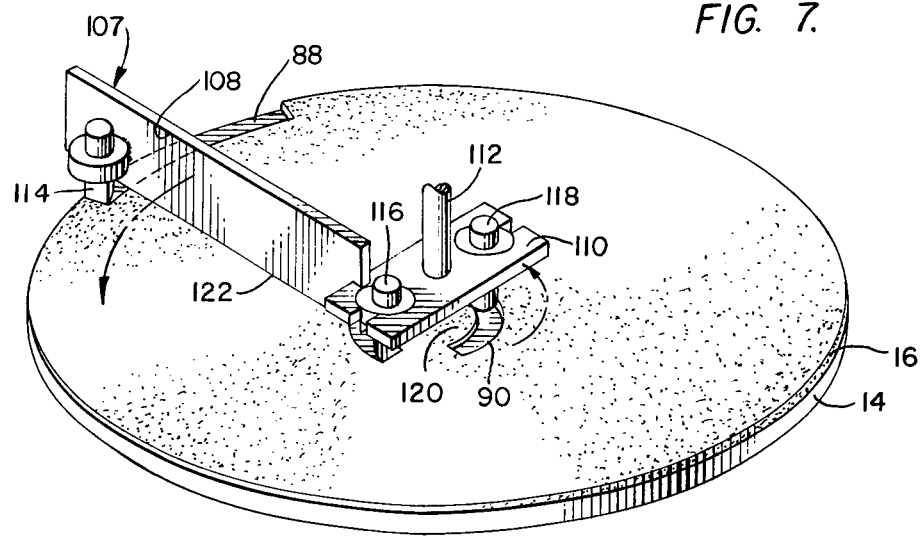
FIG. 7 is a perspective view of the scraper device of the present invention mounted for operation on a rotor.
Figure 8:
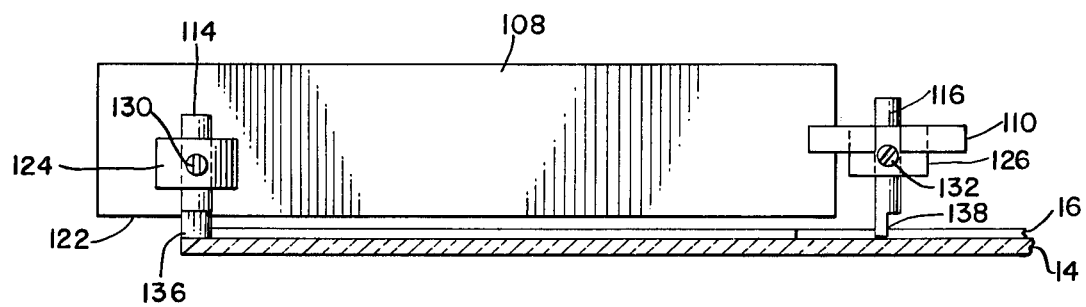
FIG. 8 is a front view of the scraper device of the present invention.
Figure 9:
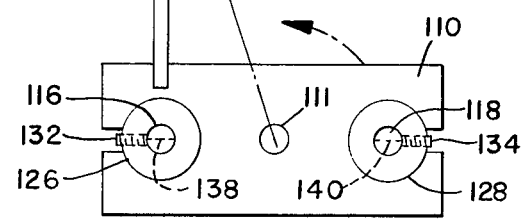
FIG. 9 is a plane view of the scraper device of the present invention.

When the preparative centrifugal chromatography device of the present invention is prepared with a slurry of absorbent material, the evenness of the coating formed on the upper surface of the rotor is improved by the use of the scraper device shown in FIGS. 7, 8 and 9. Additionally, the device is used to produce a radially graduated thickness of absorbent material on the rotor, e.g., being thicker at the axial portion of the rotor than at the circumferential portion of the rotor, yet being of uniform thickness along any circle concentric with the axis of the rotor. This graduated coating allows for the eluting components to travel outward in a radial direction at uniform speeds, despite the dispersion of the solvent and components into a greater amount of absorbent as the eluant travels radially outward.

The scraper device 107, as shown in FIGS. 7, 8 & 9, comprises a scraper blade 108 which has a scraper surface 122 formed on its lower side. The blade 108 is supported on the rotor surface at its outer end by a pin 114 adjustably fixed in collar 124, and at its inner end by a scraper brace plate assembly 110. The brace plate 110 has a central bore which allows the brace plate to fit down over the rotor shaft 112 and rest on the rotor's upper surface by means of pins 116 and 118, adjustably fixed in collars 126 and 128. All three pins can be set in a fixed position by set screws 130, 132 and 134. At the base of each pin 114, 116 and 118 is a corresponding blade edge 136, 138 and 140 which is set to face the direction of travel of the scraper device 107, which is an arc shown by the arrows in FIGS. 7 and 9. The blade edges 136, 138 and 140 effectively clear all of the absorbent coating from the rotor surface, whereas the scraper surface 123 is positioned to leave a uniform layer of absorbent on the rotor.

A graduated layer of absorbent is left on the rotor surface by the scraper blade 108 by adjusting pin 114 at a height differing from that of pins 116 and 118.

The scraper device is utilized by the following method in which known procedures are used to prepare an (uneven) absorbent layer which is then scraped to an even layer. A mixture of the powdered absorbent (silica gel, alumina, etc.) together with a binder (calcium sulfate, polyvinyl alcohol, sodium silicate, etc.) is mixed with water and poured onto a rotor having an accurately flat surface. After setting and drying, a scraping device is placed on the rotor shaft. The scraper is then pressed against the absorbent layer and rotated, thereby scraping the absorbent layer down to a thickness determined by the setting of the three adjustable pins. Any absorbent remaining within the central area and at the outer edge is removed by hand scraping thus forming the absorbent layer. The layer may be of the same thickness at all points or may be of graduated thickness, e.g., 3 mm at the inner edge and 1 mm at the outer edge, depending on the setting of the adjustable pins.

EXAMPLE

A rotor of 6 ½ (16.5 mm) diameter was coated with a 1 mm annular layer of silica gel with calcium sulfate (15%) as binder, as described above, and placed within the apparatus. With the rotor turning at 700 rpm, dichloromethane was introduced at 2 ml per min. via the solvent entrance device and the exit tube was connected to an ultraviolet absorption detector. After 5 min. for equilibration, a solution of 10 mg. of azobenzene and 10 mg. of acetone 2,4-dinitrophenylhydrazone in 0.5 ml. of dichloromethane was introduced at the entrance device. The two colored compounds were observed to separate into concentric colored circular bands which were eluted, recorded by the detector, and collected separately.

After completion of the separation, the dichloromethane and traces of impurities remaining in the absorbent were removed by adding acetone at 3 ml. per min. for 10 min. via the entrance device. The acetone remaining on the rotor was then evaporated by passing dry nitrogen into the device at a rate of 4 liters per min. for 30 min. The device was then ready for further separations.

Having fully described the invention by way of illustration and not limitation, it is understood that the device as described can be used for separatory processes other than chromatographic separations and that these other separatory functions are within the scope and contemplation of the invention; I claim:

1. A centrifugal chromatography device comprising:
   (a) a chamber;
   (b) a rotor mounted for rotation within said chamber and canted at an angle to the horizontal plane, said rotor consisting of a generally flat disc;
   (c) an absorbent medium supported on the upper surface of the rotor; and
   (d) an annular collection means canted at an angle to the horizontal plane and positioned within the chamber adjacent the outer edge of the rotor, said collection means having a deflection surface at the radially outer wall of the collection means which deflection surface is canted toward the axis of the rotor at an angle less than 90° to the upper surface of said rotor.

2. The apparatus of claim 1 wherein the annular collection means is canted at an angle in the range of 15° to 25° to the horizontal plane.

3. The apparatus of claim 1 wherein the annular collection means comprises a trough formed in the radially inner surface of the wall of the chamber.

4. The apparatus of claim 1 wherein the annular collection means comprises a trough of sheet material with a "U" shaped cross section and positioned radially inward of the wall of the chamber.

5. The apparatus of claim 1 wherein the annular collection means comprises an annular band consisting of a deflection surface canted toward the axis of the rotor at an angle less than 90° to the upper surface of said rotor.

6. The apparatus of claim 1 wherein the annular collection means includes a drain tube for removing eluted fractions located at the lowest point of the said collection means.

7. The apparatus of claim 1 wherein the centrifugal chromatography device includes means for supplying material to be separated and a carrier for eluting said material to the absorbent medium near the axis of rotation of said rotor.

8. The apparatus of claim 1 wherein the deflection surface of the annular collection means is aligned at an angle in the range of 45° to 60° to the upper surface of the rotor.

9. A centrifugal chromatography device comprising:
   (a) a chamber;
   (b) a series of rotors axially spaced from each other and mounted for rotation about a common axis within the chamber;
   (c) an absorbent medium supported on the upper surface of each rotor;
   (d) a series of annular collection means canted at an angle to the horizontal and axially spaced from each other so as to be adjacent the outer edge of a corresponding rotor; and
   (e) means for removing separated material and carrier from each of the upper annular collection means individually and directing it individually to the absorbent medium near the axis of rotation of the corresponding next lower rotor, and means for removing the separated material and carrier from the lowest collecting means.

10. The apparatus of claim 9 wherein the annular collection means are inclined at an angle in the range of 15° to 25° to the horizontal plane.

11. The apparatus of claim 9 wherein the collection means comprises a series of troughs formed in the radially inner surface of the wall of the annular chamber.

12. The apparatus of claim 9 wherein the collection means comprise a series of troughs of sheet material with "U" shaped cross sections and positioned radially inward of the wall of the annular chamber.

13. The apparatus of claim 9 wherein the collection means comprise a series of annular bands, each band consisting of a deflection surface canted toward the axis of the rotor at an angle less than 90° to the upper surface of said rotor.

14. The apparatus of claim 9 wherein each collection means includes a deflection surface at the radially outer wall of the collection means which is canted toward the axis of the rotors at an angle less than 90° to the upper surface of each of said rotors.

15. The apparatus of claim 9 wherein each collection means includes a deflection surface at the radially outer wall of the collection means which is canted toward the axis of the rotors at an angle in the range of 45° to 60° to the upper surface of the corresponding juxtapositioned rotors.

16. In the method of separating and collecting components of a mixture by centrifugal chromatography the steps of:
   (a) applying a mixture to be separated to the central area of a rotor mounted for rotation and subsequently applying a carrier for the mixture to the rotor;
   (b) separating the mixture by means of differential migration of the components of the mixture through an absorbent medium on the rotating rotor utilizing centrifugal force;
   (c) deflecting the eluted components down into an annular collection trough which is canted at an angle to the horizontal plane by means of a deflection surface as the eluted components are thrown off the rotating rotor; and
   (d) draining the collected components from the annular collection trough by the effect of gravity.

17. In combination, a chromatographic scraper device for the preparation of absorbent layer surfaces on chromatographic rotors, comprising:
   (a) a scraper blade;
   (b) a support pin, adjustably mounted at one end of said scraper blade;
   (c) a scraper brace plate attached to the opposite end of said scraper blade from said pin, said plate adjustably mounted on support pins and having a central bore;
   (d) a generally flat disc-shaped rotor having an axial shaft which engages the central bore of said scraper brace plate; said scraper blade; support pin and scraper brace plate temporarily affixed to said rotor such that the scraper blade can be positioned between a point at the circumferential edge of the rotor and a point at a radius near the axis of said rotor and rotated about the shaft of said rotor.

18. The apparatus of claim 17 in which the pins have blade edges which are adjustably aligned to face the direction of rotation of the scraper device.

* * * * *